United States Patent [19]
Marui et al.

[11] Patent Number: 4,742,001
[45] Date of Patent: May 3, 1988

[54] METHOD OF TERMINATING ISOCITRATE DEHYDROGENASE REACTION IN AN ANALYTICAL SYSTEM

[75] Inventors: Yoji Marui; Takashi Nakano, both of Ousaka; Chozo Hayashi, Hyogo; Tuyosi Fujita, Ousaka; Isamu Takagahara, Hyogo, all of Japan

[73] Assignee: Oriental Yeast Co. Ltd., Tokyo, Japan

[21] Appl. No.: 856,440

[22] Filed: Apr. 22, 1986

[30] Foreign Application Priority Data

Apr. 26, 1985 [JP] Japan .................................. 60-88850

[51] Int. Cl.$^4$ .............................................. C12Q 1/32
[52] U.S. Cl. ......................................... 435/26; 435/12
[58] Field of Search ........................................... 435/26

[56] References Cited

U.S. PATENT DOCUMENTS 3,331,752 7/1967 Struck .................................... 435/26
4,427,771 1/1984 Misaki et al. .......................... 435/26
4,622,296 11/1986 Yamanishi et al. ................... 435/26

*Primary Examiner*—Sam Rosen
*Attorney, Agent, or Firm*—Browdy & Neimark

[57] ABSTRACT

Urea, creatinine, creatine, triglycerides, or the like in a specimen can be accurately determined by terminating an isocitrate dehydrogenase reaction by addition of ATP and/or a chelating agent in a system wherein NAD+ formed from NADH is reproduced into NADH in the conjoint presence of an isocitrate, metallic ions such as magnesium or manganese ions, and isocitrate dehydrogenase in assaying a substance by means of a reaction of NADH to NAD+.

2 Claims, 1 Drawing Sheet

METHOD OF TERMINATING ISOCITRATE DEHYDROGENASE REACTION IN AN ANALYTICAL SYSTEM

DETAILED DESCRIPTION OF THE INVENTION

The present invention relates to a method of terminating an isocitrate dehydrogenase reaction in a system of NADH (nicotinamide adenine dinucleotide of reduced type) ⇌NAD+ (nicotinamide adenine dinucleotide of oxidized type) which is employed in assaying various substances in a specimen or in measuring activities of various enzymes.

More specifically, the present invention relates to a method of terminating an isocitrate dehydrogenase reaction in an NADH⇌NAD+ system to convert the system to an NADH→NAD+ system.

Figure 1:
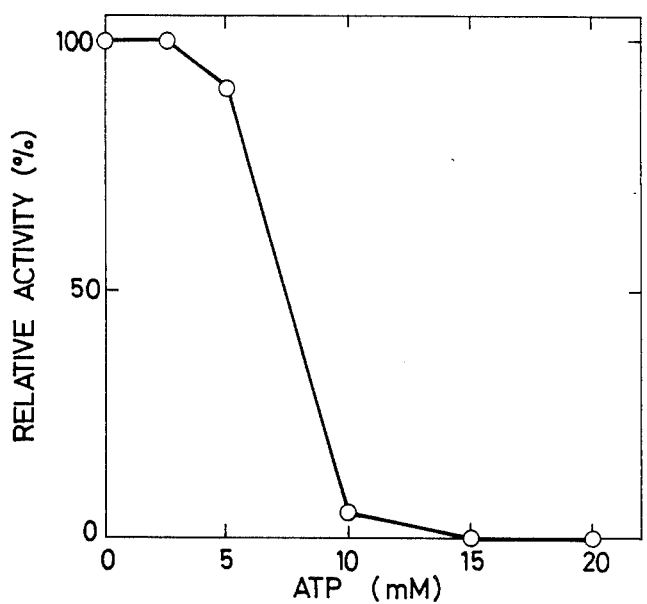
FIG. 1 is a diagram showing the influence of the ATP concentration on the iCDH activity.

It is a common practice to detect urea, creatinine, creatine, guanine, adenosine, or the like generally present in a specimen such as urine or blood and to measure the activities of various enzymes concerned with substances as mentioned just above.

In the detection and enzymatic reactions of such substances, ammonia is formed, and the formed ammonia is converted into glutamic acid with the aid of GlDH (glutamate dehydrogenase). In this case, the amount of NADH decreased in the coupled reaction of NADH→NAD+ is determined by measuring absorption at 340 nm.

Since ammonia is yielded in this reaction system without fail, ammonia originally present in a specimen is involved in the measurement so that a difficulty is experienced in accurate determination.

This problem may be solved if only ammonia originally present in the specimen is preliminarily reacted with α-KG (α-ketoglutaric acid) with the aid of GlDH to convert the ammonia into glutamic acid. Since the system of ammonia→glutamic acid is accompanied by the conversion of NADH→NAD+, NADH must be reproduced according to the reverse reaction of NAD+→NADH. In this case, a coupled reaction may be caused with isocitric acid as a substrate in the presence of iCDH (isocitrate dehydrogenase) and metallic ions such as magnesium or manganese ions. This reaction system can be expressed by the following formula (I).

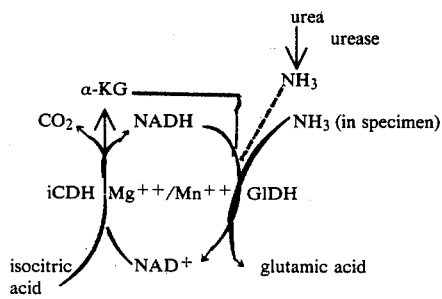

(I)

As shown in formula (I), consumption of ammonia in a specimen and assay of ammonia formed by decomposition of urea can be made according to the same coupled reaction. Accurate determination of ammonia formed by decomposition of urea can be performed for the just time after consumption of ammonia in the specimen is completed and the reaction of NAD+→NADH is completely terminated.

Therefore, the problem has been how to completely terminate the reaction of NAD+→NADH in the system of NADH⇌NAD+ in formula (I). It has not heretofore been known to completely terminate only the reaction of NAD+→NADH.

It is a common practice to assay triglycerides in a specimen such as blood and to measure the activities of GOT (glutamic acid - oxaloacetic acid transaminase) and GPT (glutamic acid - pyruvic acid transaminase).

In the detection of triglycerides and various enzymatic reactions, pyruvic acid is formed at the final stage, and the formed pyruvic acid is converted into lactic acid with the aid of LDH (lactate dehydrogenase). The amount of NADH decreased by the coupled reaction of NADH→NAD+ in such conversion was determined by measuring absorption at 340 nm.

However, since pyruvic acid is yielded without fail in this reaction system, pyruvic acid and free glycerol originally present in a specimen are involved in the measurement. Thus, a difficulty has been experienced in performing accurate determination.

No problem may be involved if pyruvic acid originally present in the specimen is converted into lactic acid with the aid of LDH in a pretreatment. Since the system of pyruvic acid→lactic acid is accompanied by the conversion of NADH→NAD+, NADH must be reproduced according to the reverse reaction of NAD+→NADH. In this case, a coupled reaction may be caused with isocitric acid as a substrate in the presence of iCDH and metallic ions such as magnesium or manganese ions. This reaction system can be expressed by the following formula (II).

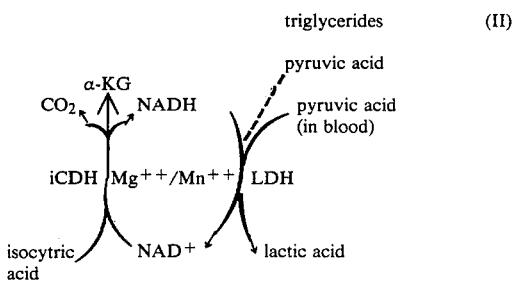

(II)

As shown in formula (II), consumption of pyruvic acid and free glycerol in a specimen and assay of pyruvic acid formed from triglycerides can be made according to the same coupled reaction. Accurate determination of pyruvic acid formed from triglycerides can be performed for the first time after consumption of pyruvic acid in the specimen is completed and the reaction of NAD+→NADH is completely terminated.

Therefore, the problem has been how to terminate the reaction of NAD+→NADH in the system of NADH⇌NAD+ in formula (II). It has not heretofore been known to completely terminate only the reaction of NAD+→NADH.

As a result of intensive investigations with a view to developing a method of completely terminating only a reaction of

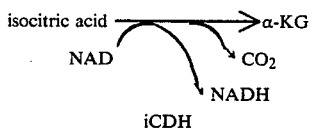

in the above-mentioned formulae (I) and (II), the inventors of the present invention have succeeded in completely terminating the reaction of isocitric acid

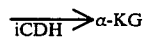

by addition of ATP and/or a chelating agent.

The present invention provides a method of terminating an iCDH reaction in assaying a substance according to the reaction of NADH to NAD+, characterized by terminating an iCDH reaction by adding ATP and/or a chelating agent in a system of reproduction of NADH from NAD+ formed from NADH in the conjoint presence of an isocitrate, metallic ions such as magnesium or manganese ions, and iCDH.

Metallic ions usable herein include those of magnesium, manganese, iron, copper, zinc, tin, and calcium. However, usable metallic ions are not limited to those ionic species mentioned above.

Usable chelating agents include EDTA and its salts, 1,2-bis(0-aminophenoxy)ethane-N,N,N',-N'-tetracetic acid and its salts, trans-1,2-cyclohexanediamine-N,N,N',N'-tetraacetic acid and its salts, dihydroxyethylglycine and its salts, 1,3-diaminopropanol-N,N,N',N'-tetraacetic acid and its salts, diethylenetriamine-pentaacetic acid and its salts, ethylenediamine-di-O-hydroxyphenylacetic acid and its salts, ethylenediaminediacetic acid and its salts ethylenediaminedipropionic acid and its salts, hydroxyethylethylenediaminetriacetic acid and its salts, ethylenediaminetetrakis(methylenephosphonic acid) and its salts, glycol-etherdiaminetetraacetic acid and its salts, hydroxyethyliminodiacetic acid and its salts, iminodiacetic acid and its salts, diaminopropanetetraacetic acid and its salts, nitrilotriacetic acid and its salts, nitrilotripropionic acid and its salts, nitrilotris(methylenephosphonic acid) and its salts, and triethylenetetraminehexaacetic acid and its salts. However, usable chelating agents are not limited to those chelating agents mentioned above.

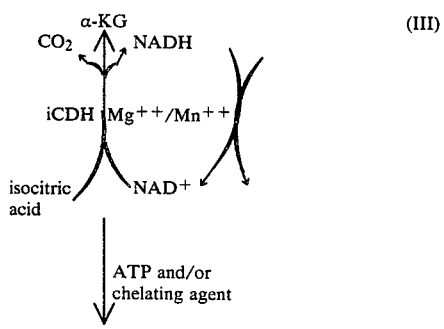

(III)

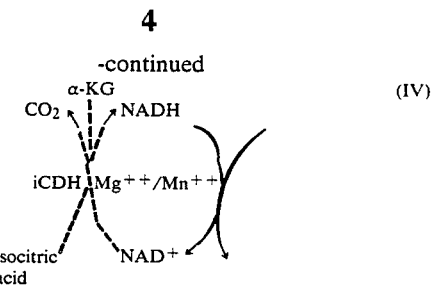

(IV)

According to the present invention, a conversion of formula (III)→formula (IV) as mentioned above is made by addition of ATP and/or a chelating agent. More specifically, complete consumption of ammonia or pyruvic acid in a specimen is effected according to formula (III), followed by addition of ATP and/or a chelating agent to the reaction system to terminate the reaction of NAD+→NADH, while, thereafter, a substance to be assayed in the specimen is decomposed and NADH is consumed by the reaction of NADH→NAD+ to perform accurate assay of the specimen. The termination of the iCDH reaction by ATP and/or chelating agent according to the present invention is very beneficial in that various reactions can be carried out in a medium as it is after the termination of the reaction by utilizing the reaction of NADH→NAD+.

The amount of ATP to be added to the reaction system may be 15 mM or more. FIG. 1 is a diagram showing the influence of the ATP concentration on the iCDH activity. It is understood that iCDH completely loses its activity at an ATP concentration of 15 mM or higher.

Figure 2:
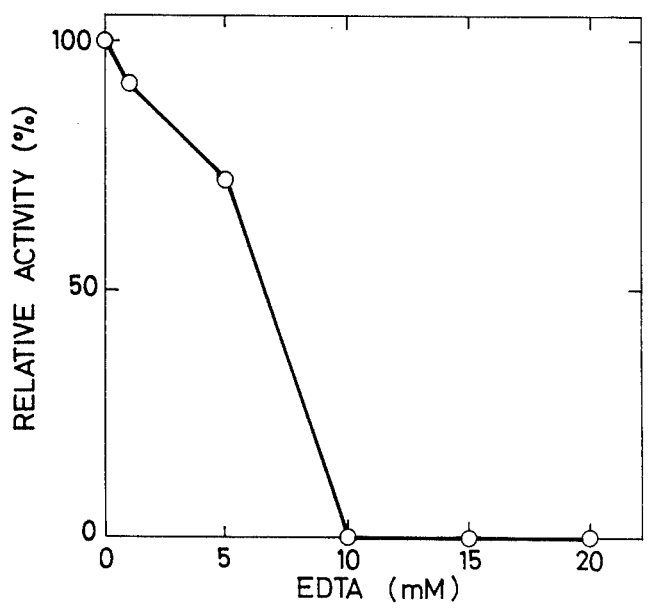
FIG. 2 is a diagram showing the influence of the EDTA concentration on the iCDH activity.

The amount of a chelating agent, for example, EDTA, to be added to the reaction system may be 10 mM or more. FIG. 2 is a diagram showing the influence of the EDTA concentration on the iCDH activity. It is understood that iCDH completely loses its activity at a concentration of 10 mM or higher.

The method of terminating an iCDH reaction according to the present invention can be utilized in assaying a substance which yields ammonia upon decomposition thereof and in measuring the activity of an enzyme associated therewith. It can also be utilized in assaying a substance which produces pyruvic acid upon decomposition thereof and in measuring the activity of an enzyme associated therewith.

Specific examples of application of the present invention include the following methods of assaying respective urea, creatinine, creatine, and triglycerides.

(A) Method of Assaying Urea

GlDH, α-KG, NADH (or NADPH), isocitric acid, metallic ions such as magnesium or manganese ions, and iCDH are admixed with a specimen to consume ammonia originally present in the specimen. Subsequently, ATP and/or a chelating agent is added to terminate the iCDH reaction, while, simultaneously or thereafter, urease is added to produce ammonia, which is determined to assay urea.

This reaction system can be expressed by the following formula (a).

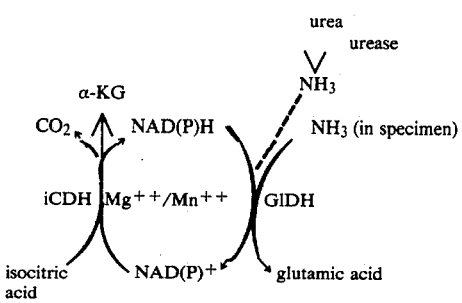

As shown in formula (a), consumption of ammonia in the specimen and assay of ammonia formed by decomposition can be made according to the same coupled reaction. Accurate assay of ammonia formed by decomposition of urea can be performed for the first time after consumption of ammonia in the specimen is completed and the reaction of NAD(P)+→NAD(P)H is completely terminated.

(B) Method of Assaying Creatinine

GlDH, α-KG, NADH (or NADPH), isocitric acid, metallic ions such as magnesium or manganese ions, and iCDH are admixed with a specimen to consume ammonia originally present in the specimen. Subsequently, ATP and/or a chelating agent is added to terminate the iCDH reaction, while, simultaneously or thereafter, creatininase is added to produce ammonia, which is determined to assay creatinine.

This reaction system can be expressed by the following formula (b).

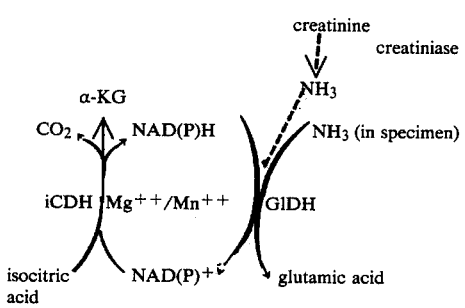

As shown in formula (b), consumption of ammonia in the specimen and assay of ammonia formed by decomposition can be made according to the same coupled reaction. Accurate assay of ammonia formed by decomposition of creatinine can be performed for the first time after consumption of ammonia in the specimen is completed and the reaction of NAD(P)+→NAD(P)H is completely terminated.

(C) Method of Assaying Creatine

GlDH, α-KG, NAD(P)H, isocitric acid, metallic ions such as magnesium or manganese ions, creatinine deiminase, and iCDH are admixed with a specimen to consume ammonia and creatinine originally present in the specimen. Subsequently, ATP and/or a chelating agent is added to terminate the iCDH reaction, while, simultaneously or thereafter, creatininase is added to produce ammonia, which is determined to assay creatine.

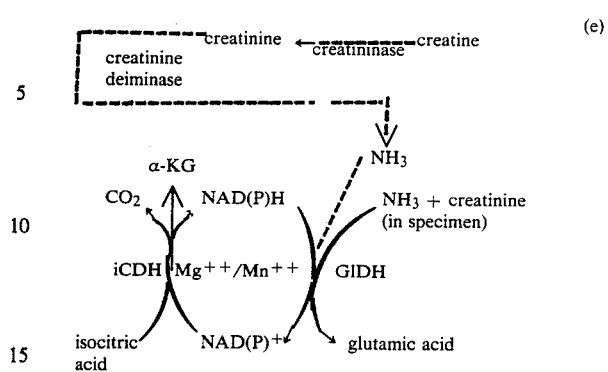

As shown in formula (c), assay of free creatine in the specimen can be made according to the same coupled reaction as in consumption of creatinine and ammonia in the specimen. Accurate assay of ammonia formed by decomposition of creatine can be performed for the first time after consumption of creatinine and ammonia in the specimen is completed and the reaction of NAD(P)+→NAD(P)H is completely terminated.

(D) Method of Assaying Triglycerides

LDH, NADH, ATP, PEP, glycerokinase, pyruvate kinase, isocitric acid, metallic ions such as magnesium or manganese ions, and iCDH are admixed with a specimen containing triglycerides to consume glycerol originally present in the specimen. Subsequently, ATP is added to terminate the iCDH reaction, while, simultaneously or thereafter, lipase is added to produce pyruvic acid, which is determined to assay the triglycerides.

This reaction system can be expressed by the following formula (d).

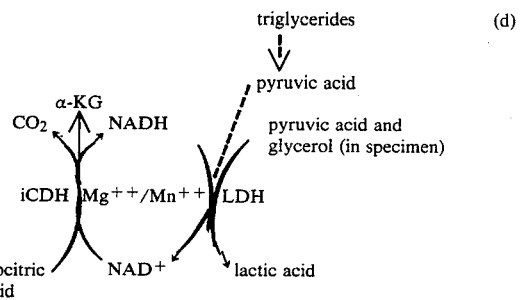

As shown in formula (d), consumption of free pyruvic acid and glycerol and assay of pyruvic acid formed from triglycerides can be made according to the same coupled reaction. Accurate assay of pyruvic acid formed from triglycerides can be performed for the first time after consumption of pyruvic acid and free glycerol originally present in the specimen is completed and the reaction of NAD+→NADH is completely terminated.

Examples according to the present invention will now be described.

EXAMPLE 1

MgCl: 5 mM
isocitric acid: 2 mM
NAD$^{30}$: 1 mM
AMP: 0.5 mM

A varied amount of ATP was added to 3 ml of a 0.1 M Tris hydrochloride buffer solution (pH: 8.0) containing the above-listed ingredients to provide an ATP concentration of 0 to 20 mM. Each of the resulting mixtures was kept at a temperature of 25° C., and admixed with 20 μl of iCDH of about 3 u/ml, followed by measurement of the iCDH activity based on an increase in absorption at 340 nm by spectrophotometry.

The results are shown in FIG. 1.

EXAMPLE 2

MgCl: 1 mM
isocitric acid: 2 mM
NAD+: 1 mM
AMP: 0.5 mM

A varied amount of EDTA was added to 3 ml of a 0.1 M Tris hydrochloride buffer solution (pH: 8.0) containing the above-listed ingredients to provide an EDTA concentration of 0 to 20 mM. Each of the resulting mixtures was kept at a temperature of 25° C., and admixed with 20 μl of iCDH of about 3 u/ml, followed by measurement of the iCDH activity based on an increase in absorption at 340 nm by spectrophotometry.

The results are shown in FIG. 2.

EXAMPLE 3

(Determination of urea)

α-KG: 10 mM
NADH: 0.16 mM
isocitric acid: 5 mM
ADP: 0.5 mM
MgCl$_2$: 1 mM
GlDH: 100 u/ml
iCDH: 2 u/ml 30 μl each of specimens containing urea and 160 mM of ammonia and having a varied concentration of 0 to 1,000 mg/dl in terms of nitrogen in urea form was added to 2.4 ml of a 0.1 M phosphate buffer solution (pH: 7.5) containing the above-listed ingredients. Each of the resulting mixtures was kept at a temperature of 37° C. for 5 minutes, and admixed with 0.6 ml of a solution of a mixture of ATP and urease to provide ATP and urease concentrations of 20 mM and 0.1 u/ml, respectively, followed by determination of nitrogen in urea form in the specimen based on a decrease in absorption at 340 nm at 25° C. for 1 minute by spectrophotometry. The results are shown below.

| Specimen No. | 1 | 2 | 3 | 4 | 5 | 6 | 7 | 8 | 9 | 10 | 11 |
|---|---|---|---|---|---|---|---|---|---|---|---|
| Calcd. value of N in urea form (mg/dl) | 1,000 | 900 | 800 | 700 | 600 | 500 | 400 | 300 | 200 | 100 | 0 |
| Measured value (mg/dl) | 718 | 710 | 700 | 665 | 590 | 498 | 403 | 301 | 200 | 100 | 0 |

EXAMPLE 4

(Determination of creatinine)

α-KG: 10 mM
NADH: 0.16 mM
isocitric acid: 5 mM
ADP: 0.5 mM
MgCl$_2$: 0.5 mM
GlDH: 50 u/ml
iCDH: 2 u/ml 30 μl each of creatinine-containing specimens containing 150 mM of ammonia and having a varied creatinine concentration of 0 to 100 mg/dl was added to 2.4 ml of a 0.1 M triethanolamine hydrochloride solution (pH: 7.5) containing the above-listed ingredients. Each of the resulting mixtures was kept at a temperature of 37° C. for 5 minutes, and admixed with 0.6 ml of a solution of a mixture of ATP and creatininase to provide ATP and creatininase concentrations of 20 mM and 0.3 u/ml, respectively, followed by determination of creatinine in the specimen based on a decrease in absorption at 340 nm at 37° C. for 1 minute by spectrophotometry. The results are shown below.

| Specimen No. | 1 | 2 | 3 | 4 | 5 | 6 | 7 | 9 | 10 | 11 |
|---|---|---|---|---|---|---|---|---|---|---|
| Calcd. value of creatinine (mg/dl) | 100 | 90 | 80 | 70 | 60 | 50 | 40 | 30 | 20 | 0 |
| Measured value (mg/dl) | 101 | 90 | 79 | 68 | 62 | 51 | 39 | 30 | 22 | 0 |

EXAMPLE 5

α-KG: 10 mM
NADH: 0.16 mM
isocitric acid: 5 mM
ADP: 0.5 mM
MgCl$_2$: 0.5 mM
GlDH: 50 u/ml
iCDH: 2 u/ml
creatinine deiminase: 5 u/ml 30 μl each of creatine-containing specimens containing 100 mg/dl of creatinine and 100 mM of ammonia and having a varied creatine concentration of 0 to 20 mg/dl was added to 2.4 ml of a 0.1 M triethanolamine hydrochloride solution (pH; 7.5) containing the above-listed ingredients. Each of the resulting mixtures was kept at a temperature of 37° C. for 5 minutes, and admixed with 0.6 ml of a solution of a mixture of ATP and creatininase to provide ATP and creatininase concentrations of 20 mM and 1 u/ml, respectively, followed by determination of creatine in the specimen based on a decrease in absorption at 340 nm at 37° C. for 1 minute by spectrophotometry. The results are shown below.

| Specimen No. | 1 | 2 | 3 | 4 | 5 | 6 | 7 | 9 | 10 | 11 |
|---|---|---|---|---|---|---|---|---|---|---|
| Calcd. value of creatine (mg/dl) | 20.0 | 17.5 | 15.0 | 12.5 | 10.0 | 8.0 | 6.0 | 4.0 | 2.0 | 0 |
| Measured value (mg/dl) | 19.8 | 17.9 | 15.1 | 11.9 | 10.3 | 8.2 | 5.9 | 4.0 | 1.8 | 0 |

EXAMPLE 6

(Determination of triglycerides)

KCl: 100 mM
MgSO$_4$: 3 mg

ATP: 1 mM
phosphoenolpyruvic acid: 1.5 mM
isocitric acid: 5 mM
NADH: 0.2 mM
LDH: 6 u/ml
pyruvate kinase: 30 u/ml
glycerokinase: 2 u/ml
iCDH: 2 u/ml 20 μl each of triglyceride (TG)-containing specimens containing 50 mM of glycerol and having a varied TG concentration (A=50 mg/dl, B=100 mg/dl, C=300 mg/dl, D=500 mg/dl, and E=750 mg/dl) was added to 2.9 ml of a 0.1 M triethanolamine hydrochloride solution (pH: 7.5) containing the above-listed ingredients. Each of the resulting mixtures was kept at a temperature of 37° C. for 10 minutes, and admixed with 100 μl of a solution of a mixture of ATP and lipase to provide ATP and lipase concentrations of 20 mM and 5,000 u/ml, respectively, followed by measurement of a decrease in absorbance at 340 nm at 37° C. by spectrophotometry.

The values of ΔE were as follows:

A=0.023, B=0.046, C=0.139, D=0.235, E=0.351

As a result of calculation according to the following equation, it was found that glycerol originally present in every specimen was so completely eliminated that determination of the triglyceride content in every specimen could be made without any influences of the above-mentioned glycerol on the determination.

Triglyceride content $$mg/dl = \frac{\Delta E}{6.2} \times \frac{3.02}{0.02} \times \frac{885}{1000} \times 100$$

ΔE=change in absorbance due to decrease of NADH
6.2=absorbance of 1 mM of NADH
3.02=total volume of reaction mixture
0.02=volume of specimen
885=molecular weight of triolein

What is claimed is:

1. A method of terminating an isocitrate dehydrogenase reaction in an analytical system wherein NAD+ formed from NADH is reproduced into NADH in the conjoint presence of an isocitrate, metallic ions, and isocitrate dehydrogenase in assaying a substance by means of a reaction of NADH to NAD+, which comprises terminating the isocitrate dehydrogenase reaction by adding ATP and/or a chelating agent to the reaction system.

2. A method according to claim 1 wherein said metallic ions are magnesium or manganese ions.

* * * * *